US007067791B2

(12) United States Patent
Sagatelyan et al.

(10) Patent No.: US 7,067,791 B2
(45) Date of Patent: Jun. 27, 2006

(54) SYSTEM AND METHODS FOR DYNAMIC RANGE EXTENSION USING VARIABLE LENGTH INTEGRATION TIME SAMPLING

(75) Inventors: Dmitry M. Sagatelyan, Alameda, CA (US); Tor Slettnes, Castro Valley, CA (US)

(73) Assignee: Applera Cororation, Foster City, CA (US)

( * ) Notice: Subject to any disclaimer, the term of this patent is extended or adjusted under 35 U.S.C. 154(b) by 0 days.

(21) Appl. No.: 11/059,740

(22) Filed: Feb. 17, 2005

(65) Prior Publication Data

US 2005/0145780 A1    Jul. 7, 2005

Related U.S. Application Data

(62) Division of application No. 10/271,477, filed on Oct. 15, 2002, now Pat. No. 6,894,264.

(51) Int. Cl.
*H01J 40/14* (2006.01)

(52) U.S. Cl. ............................. 250/214 R; 250/214.1

(58) Field of Classification Search ............ 250/214.1, 250/208.1, 214 R; 348/307–309, 311–312, 348/316, 317, 319–323
See application file for complete search history.

(56) References Cited

U.S. PATENT DOCUMENTS

| 5,194,957 | A |   | 3/1993  | Kyuma |            |
|-----------|---|---|---------|-------|------------|
| 5,200,623 | A | * | 4/1993  | Cannata | 250/338.1 |
| 5,416,611 | A | * | 5/1995  | Tandon | 250/208.1 |
| 6,008,486 | A |   | 12/1999 | Stam et al. | |
| 6,014,213 | A | * | 1/2000  | Waterhouse et al. | 356/344 |
| 6,040,586 | A |   | 3/2000  | Slettnes | |
| 6,115,065 | A | * | 9/2000  | Yadid-Pecht et al. | 348/308 |
| 6,538,593 | B1| * | 3/2003  | Yang et al. | 341/155 |
| 6,831,689 | B1| * | 12/2004 | Yadid-Pecht | 348/297 |
| 2002/0122126 | A1 | | 9/2002 | Lenz | |

OTHER PUBLICATIONS

Yadid-Pecht, Orly, "Wide-dynamic-range sensors," *Optical Engineering*, vol. 38, No. 10, Oct. 1999, pp. 1650-1659.

* cited by examiner

*Primary Examiner*—Que T. Le
(74) *Attorney, Agent, or Firm*—Knobbe Martens Olson & Bear, LLP

(57) ABSTRACT

A photo-detector generated signal is measured as a sample set comprising a long signal and a short signal. The short signal is scaled to the value of the long signal if the long signal exceeds a dynamic range associated with the photo detector. In one embodiment, the short signal is obtained during a short time interval that is at the approximate middle of a long time interval such that the short and long intervals share a common median time value. Given such symmetry, an approximately linear signal yields a proportionality parameter between the long and short signals thereby allowing the short signal to be scaled. The proportionality parameter facilitates determination of an integration independent component of the photo detector signal that should be removed from the measured long and short signals before scaling. A plurality of sample sets can also be processed such that each sample set overlaps with its neighboring sample set, thereby increasing the effective number of sample sets.

8 Claims, 7 Drawing Sheets

CCD signal 125

Software controlled sampling method 134  136
Long  Short  Long  Short  Long  Short → Time Integration time = $T_L$  $T_S$  $T_L$  $T_S$  $T_L$  $T_S$ Integral of actual signal = $A_L$   $A_S$ Integration independent noise = C   C Integral of measured signal = L   S $L = A_L + C$
$S = A_S + C$           $C = S - (L-S)/(K-1)$
$A_L/A_S = K$           Where K = proportionality parameter One embodiment of sample set

US 7,067,791 B2

SYSTEM AND METHODS FOR DYNAMIC RANGE EXTENSION USING VARIABLE LENGTH INTEGRATION TIME SAMPLING

RELATED APPLICATION

This application is a divisional of U.S. patent application Ser. No. 10/271,477, filed on Oct. 15, 2002 now U.S. Pat. No. 6,894,264, entitled "SYSTEM AND METHODS FOR DYNAMIC RANGE EXTENSION USING VARIABLE LENGTH INTEGRATION TIME SAMPLING" which is hereby incorporated in its entirety herein.

BACKGROUND

1. Field

The present teachings generally relate to methods, software and apparatus useful for signal processing and, in various embodiments, to a system and method for resolving signals generated by a charge coupled device.

2. Description of the Related Art

Many photo-detectors such as charge coupled devices (CCD) are designed to detect light emissions and produce signals that can be resolved to quantify observed light intensity. Generally, conventional CCD's comprise one or more light-detecting elements that may be sensitive enough to detect as little as a few photo electrons. It is often desirable for a CCD device to possess a dynamic range of detection that extends several orders of magnitude with respect to the number of detectable photo electrons. Conventional solutions to increasing the dynamic range may include increasing the number of bits of analog-to-digital converters (ADC) associated with the CCD. This increase in the number of bits, however, also increases the cost of manufacture and processing time of the CCD. Another method for extending the dynamic range may involve splitting of the signal from a selected element into multiple signals that are hardware resolved. Each signal may further be provided with a different gain to thereby allow the split signals to collectively cover a wider dynamic range than that of a single signal. Such a hardware adaptation for dynamic range enhancement often requires costly retrofitting of the instrument and may not be practical to implement with existing devices. From the foregoing, it will be appreciated that there is a need for an alternative method by which the dynamic range of a CCD or other photo-detector device may be improved. Furthermore, there is a need for a dynamic range extension methodology that may be adapted for use with existing systems without necessitating significant hardware modifications.

SUMMARY

In various embodiments, the present teachings disclose a system and methods for improving the dynamic range of detection for a CCD-generated signal using a variable length integration time sampling approach. In one aspect, an existing signal, having a predefined sampling pattern, is restructured into a wider dynamic range signal without the need for additional dedicated hardware. One or more constructs may be utilized, each of which may offer performance benefits for particular sampling implementations. Each construct may further be adapted for use with either shuttered or shutterless CCD devices, such as those used with some of the nucleic acid sequence analysis systems.

In various embodiments, the constructs for improving the dynamic range of detection assess a signal component using a per-frame analysis approach. Each frame may comprise long and/or short samplings determined, in part, by the duration of time for which a signal is generated from incoming light. Based on the scaling characteristics, an integration-independent component (offset) of the signal may be removed to facilitate scaling of the signal.

In one aspect, the invention comprises a method for dynamic range extension during the processing of a photo-detector acquired signal, the method comprising: Acquiring a first signal component and a second signal component from a photo-detector wherein the first signal component comprises an integration of the photo-detector signal during a first time interval and wherein the second signal component comprises integration of the photo-detector signal during a second time interval wherein the second time interval is temporally proximal to and shorter than the first time interval such that the second signal component and the first signal component represent the acquired values of the photo-detector signal during a selected time period delineated by the first and second time intervals; Determining a scaling factor between the second signal component and the first signal component; Determining if the first signal component exceeds a selected dynamic range such that if the first signal component exceeds the dynamic range, scaling the second signal component by the scaling factor to approximate the first signal component; and thereafter using the scaled second signal component to represent the value of the signal during the selected time period.

In another aspect, the invention comprises a method for scaling of a signal generated by a photo-detector signal processor, the method comprising: Determining a first signal value L and a second signal value S for a sample set wherein the first signal value corresponds to a signal acquired during a first interval and wherein the second signal value corresponds to a signal acquired during a second interval, wherein the second signal value is less than the first signal value and wherein the first signal exceeds a specified range; Determining a proportionality parameter K between the first signal value and the second signal value; and Scaling the second signal value to approximate what the first signal value would be beyond the specified range.

In still another aspect, the invention comprises a method of sampling a photo-detector signal, the method comprising: Performing a series of integrations of the photo-detector signal wherein the series comprises alternating long and short integration intervals; and forming a plurality of overlapping sample sets wherein each sample set comprises integrations performed during at least one long interval to yield a first signal value and at least one short interval to yield a second signal value and wherein each sample set overlaps with its neighboring sample set by at least one of the long or short intervals.

In a still further aspect, the invention comprises a system for processing a photo-detector signal associated with a sequencing apparatus, comprising: A photo-detector that detects a labeled sample signal that is transformed into an electronic signal; An electronic signal processor that acquires one or more sample sets associated with the electronic signal wherein each sample set comprises a first signal value L and a second signal value S wherein the first signal value corresponds to an integrated photo-detector signal acquired during a first interval and wherein the second signal value corresponds to an integrated photo-detector signal acquired during a second interval that is less than the first interval; and wherein the signal processor is configured to determine a proportionality parameter K between the first signal value and the second signal value such that the second signal value can be scaled to the first signal value and wherein the processor outputs a processed signal representative of the sample set based on the first and second signal values.

DETAILED DESCRIPTION OF CERTAIN EMBODIMENTS

Figure 1A:
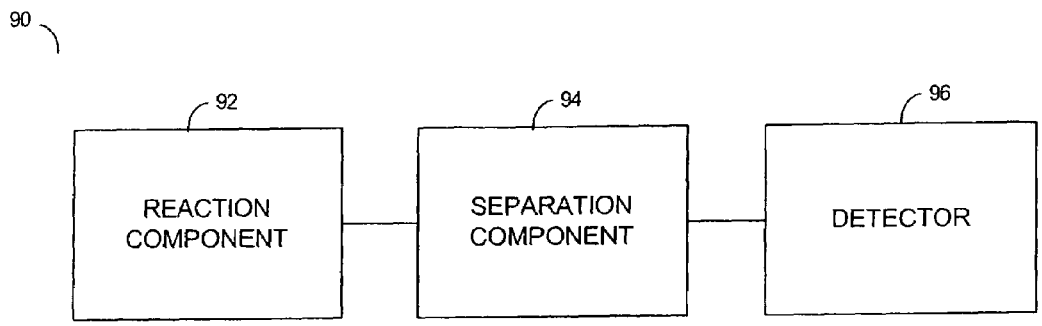
FIG. 1 illustrates an exemplary sequence analysis system incorporating a CCD label-detection component.

These and other aspects, advantages, and novel features of the present teachings will become apparent upon reading the following detailed description and upon reference to the accompanying drawings. In the drawings, similar elements have similar reference numerals.

FIG. 1A illustrates an exemplary schematic diagram for an analyzer 90 capable of sequence determination or fragment analysis for nucleic acid samples. In various embodiments, the analyzer 90 may comprise one or more components or devices that are used for labeling and identification of the samples by performing automated sequence analysis. The various components of the analyzer 90, described in greater detail hereinbelow, may comprise separate components or a singular integrated system. The present teachings may further be applied to both automatic and semi-automatic sequence analysis systems as well as to methodologies wherein some of the sequence analysis operations are manually performed.

It will further be appreciated that the dynamic range enhancement methods may be applied to numerous different types of photo and signal detection methodologies and are not necessarily limited to CCD signal detection and resolution. Additionally, although the present teachings are described in various embodiments in the context of sequence analysis, these methods may be readily adapted to other devices/instrumentation and used for purposes other than sequence analysis. For example, the present teachings may be applied to electronic telescopes and microscopes that utilize photo-detecting devices such as CCDs to improve the dynamic range and signal-to-noise ratio (SNR) of these instruments.

It will also be appreciated that the dynamic range enhancement methods may be applied to photo-detectors in general for a variety of applications, some of which are listed as examples above. Photo-detectors in general convert incident photons to electrical signals, and may include, by way example, CCDs, photomultipliers, or semiconductor based devices such as photo-diodes.

In the context of sequence analysis, the exemplary sequence analyzer 90 may comprise a reaction component 92 wherein PCR amplification or cycle sequencing of the sample is performed. Using these amplification techniques, a label such as a fluorescent or radioactive dideoxy-nucleotide may be introduced into the sample resulting in the production of a number of fragments of varying sequence lengths. As is known in the art, one or more labels or dyes may be used during the amplification step to generate distinguishable fragment populations for each base to be subsequently identified. Following amplification, the fragments may then be subjected to a separation operation using a separation component 94. In one aspect the separation component 94 comprises a gel-based or capillary electrophoresis apparatus which separates the fragments into distinguishable populations. Using this approach, electrical current may be passed through the amplified sample fragments which have been loaded into a separation matrix (e.g. polyacrylamide or agarose gel). The application of electrical current results in the migration of the sample through the matrix. As the sample migration progresses, the labeled fragments are separated and passed through a detector 96 wherein resolution of the labeled fragments is performed.

In one aspect, the detector 96 may identify various sizes or differential compositions for the fragments based on the presence of the incorporated label. In one exemplary embodiment, fragment detection may be performed by generation of a detectable signal produced by a fluorescent label that is excited by a laser tuned to the label's absorption wavelength. Energy absorbed by the label results in a fluorescence emission that corresponds to a signal measured for each fragment. By keeping track of the order of fluorescent signal appearance along with the type of label incorporated into the fragment, the sequence of the sample can be discerned. A more detailed explanation of the sequencing process is provided in commonly assigned U.S. Pat. No. 6,040,586, entitled "Method and System for Velocity-Normalized Position-Based Scanning."

Figure 1B:
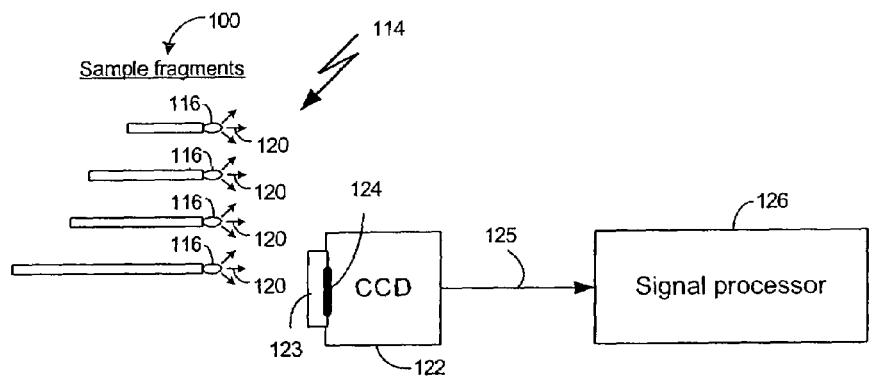

FIG. 1B, further illustrates exemplary components for the detector 96 which may be used to acquire the signal associated with a plurality of labeled fragments 100. As previously indicated, the labeled fragments 100 may be resolved by measuring the quantity of fluorescence or emitted energy generated when the fragments 100 are subjected to an excitation source 114 of the appropriate wavelength and energy (e.g. a tuned laser). The energy emissions 120 produced by a label 116 associated with the fragments 100 may be detected using a charge-coupled device (CCD) 122 as the fragments 100 pass through a detection window 123 where a plurality of energy detecting elements 124 capture at least some of the emitted energy from the label 116. In one aspect, an electronic signal 125 is generated by the CCD 122 that is approximately proportional to the relative abundance of the fragments 100 passing through the detection window 123 at the time of energy capture and the order which the fragments 100 appear in the detection window 123 may be indicative of their relative length with respect to one another.

A signal processor 126 is further configured to perform signal sampling operations to acquire the electronic signal generated by the CCD 122 in response to the fragments 100. In various embodiments, the signal processor 126 is configured to perform these sampling operations in a predetermined manner by signal acquisition over selected intervals. In many conventional signal processors, the pattern or timing of signal acquisition is limited by software and/or hardware imposed restrictions which limit the flexibility in analysis of the signal. This may further result in a limited dynamic range of signal acquisition. As will be described in greater detail hereinbelow, the present teachings may aid in overcoming some sampling limitations and provide increased flexibility in signal analysis and resolution. One desirable feature provided by various embodiments of the present teachings is the ability to utilize existing signal information in such a manner so as to improve the dynamic range of the system thereby potentially increasing its functionality.

Figure 1C:
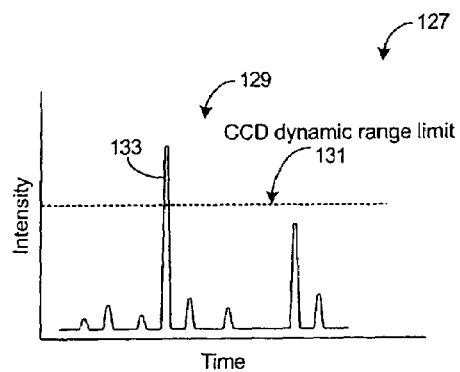

In various embodiments, the signal 125 outputted by the CCD 122 may vary significantly between sample fragments 100. This presents a potential problem in conventional systems as the signal 125 may exceed the dynamic range of the signal processor 126 associated with the CCD 122 unless compensatory measures are taken. As illustrated in the simplified electropherogram 129 shown in FIG. 1C, signals 125 may be acquired forming a signal distribution comprised of one or more signal intensity "peaks". Each peak may further be indicative of a detected fragment 100. The electropherogram 127 may further comprise a theoretical or experimental dynamic range limit 131 wherein peak intensities which exceed this limit 131 are subject to diminished accuracy in quantitation. This concept is exemplified by an exemplary peak 133 shown to exceed the dynamic range limit 131. In one aspect, if such an occurrence is left unmitigated, the quantitation and sequence resolution information arising from the peak 133 may be compromised. In various embodiments, the present teachings facilitate resolution of peak intensities which may exceed the normal signal processor tolerances and may establish a new dynamic range allowing for more accurate calculations to be performed with the available signal information.

In various embodiments, some of the information that may be determined through signal resolution and peak identification may include determination of the relative abundance or quantity of each fragment population. Evaluation of the signals may further be used to determine the sequence or composition of the sample using various known base sequence resolution techniques. It will further be appreciated by one of skill in the art that the exemplified signal distribution may represent one or more nucleic acid fragments for which the relative abundance of each fragment may be determined based, in part, upon the determination of the relative area associated with each peak. The present teachings may therefore be integrated into existing analysis approaches to facilitate peak evaluation and subsequent integration operations typically associated with sequence analysis.

In various embodiments, the analysis of the electropherogram 127 may be advantageously performed by the signal processor 126. The signal processor 126 may further be configured to execute on one or more processors. The signal processor's components may include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables. Furthermore, the signal processor 126 may output a processed signal or analysis results to other devices or instrumentation where further processing may take place.

Figure 2:
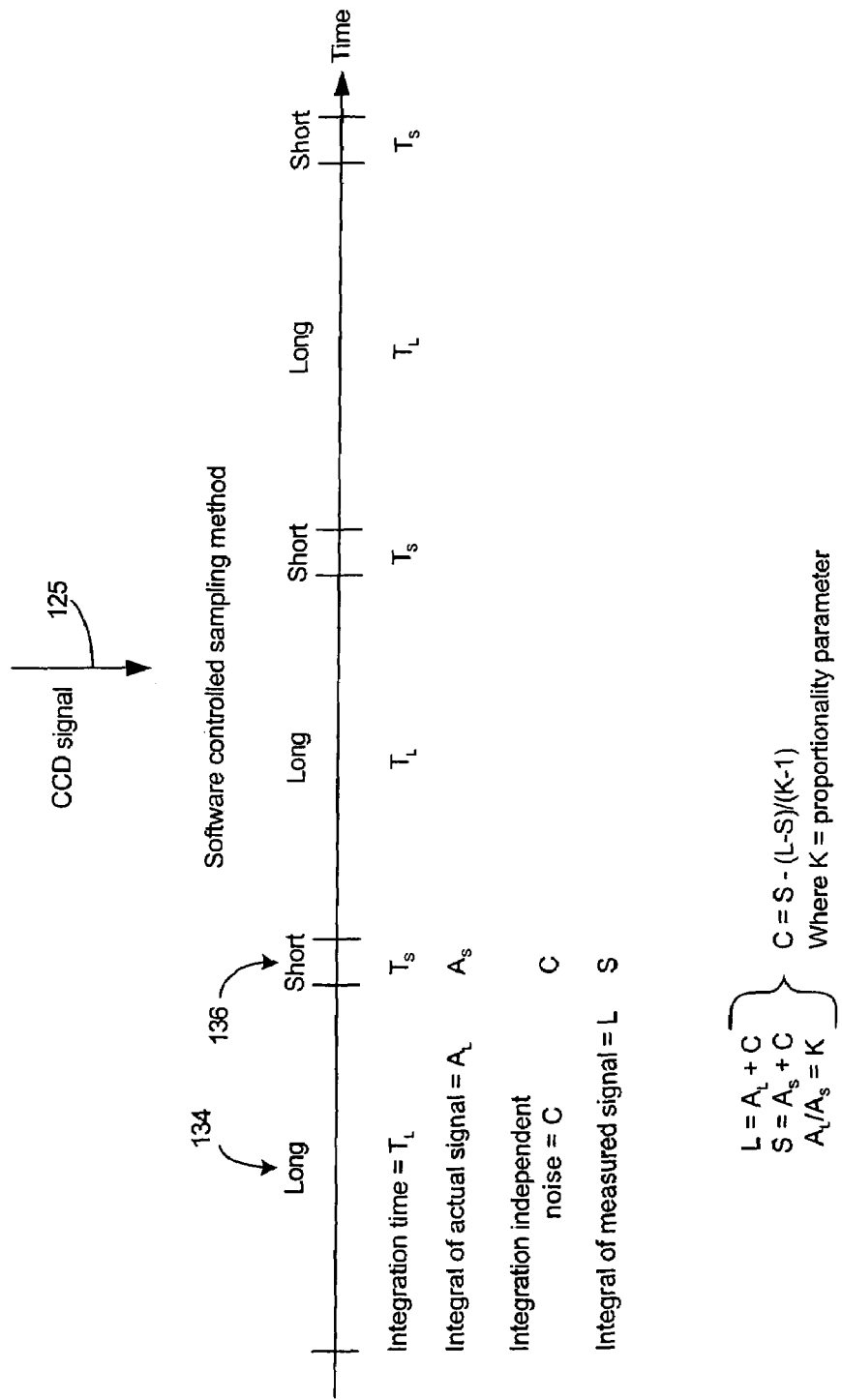
FIG. 2 illustrates an exemplary method for software sampling of a signal comprising a series of long and short intervals.

FIG. 2 illustrates one aspect of signal processing that may be implemented by the signal processor 126 described above in reference to FIG. 1A–C. In various embodiments, a software controlled sampling method comprises an alternating series of having a long sample 134 and a short sample 136. These samples 134 reflect a time period where information is actively acquired from the CCD 122. Typically, an idle time interval (also referred to as "dead time") exists between adjacent sampling intervals. In the sampling scheme illustrated in FIG. 2, an idle interval may be is interposed temporally between the long and short samples. In various embodiments, the idle interval may be substantially negligible when compared to the short or long sampling intervals. In other embodiments, the idle interval may be significant and account for an appreciable amount of the sampling time. As will be described in greater detail hereinbelow, when performing signal processing operations it may be desirable to account for idle time between signal samplings. In one aspect, identification of the idle time may be useful in improving the dynamic range of signal detection.

In various embodiments, the long sample 134 may represent an integration of the signal 125 during a time interval of $T_L$. Such an integration of the signal 125 from the CCD 122 may result in a measured signal L that includes an actual signal $A_L$ and an integration independent component C (offset). The integration independent component C includes, but is not limited to, an on-chip amplifier bias and spurious charge associated with the CCD 122. Similarly, the short sample 136 may represent an integration of the signal 125 during a time interval of $T_S$. Such an integration of the signal 125 from the CCD 122 results in a measured signal S that may include an actual signal $A_S$ and the offset C. Thus, the measured signals L and S may be expressed as $$L = A_L + C \tag{1}$$

$$S = A_S + C. \tag{2}$$

Furthermore, a relationship between the actual signals $A_L$ and $A_S$ may be expressed as $$\frac{A_L}{A_S} = K \tag{3}$$

where K is a proportionality parameter that depends on the nature of the actual signals $A_L$ and $A_S$ during their respective integration intervals $T_L$ and $T_S$.

In one aspect, it is desirable to determine the actual signals $A_L$ and $A_S$ by subtracting the offset C from the measured signals L and S, respectively. The offset C may be determined by combining Equations 1–3 to yield $$C = S - \frac{L - S}{K - 1}. \tag{4}$$

Thus, for given values of L and S, by determining the signal dependent proportionality parameter K, the offset C may be determined with Equation 4. Then the resulting offset C may be subtracted from the measured signals L and S to yield the actual signals $A_L$ and $A_S$, respectively. Once the actual signals $A_L$ and $A_S$ are determined, they may be either analyzed directly, or scaled in a manner described below.

In one aspect, a sample set comprises at least one long sample 134 and one short sample 136 that is temporally adjacent to the at least one long sample 134. As described below in greater detail, various combinations of the long and short samples may be formed to obtain such a sample set.

In one embodiment, the measured signals L and S may be obtained by directing the CCD signal 125 into a charge integrating analog to digital converter (ADC) and integrating for $T_L$ and $T_S$ respectively. In one aspect, the integrated signal may depend on the number of photo-electrons (N) generated by the CCD 122 where N obeys Poisson statistics. As is understood, relative intrinsic error associated with Poisson statistics may be expressed as $1/\sqrt{N}$. This relationship indicates that it is generally preferable for the integrated signal to be as large as possible within the dynamic range of the ADC. Thus in one aspect, long and short measurements that make up the sample set may be selectively scaled. It is generally preferable, for a given sample set where the CCD signal 125 is not relatively intense, that the long measurement is used for signal analysis if the long signal L is within the dynamic range of the ADC, since long measurements generally yield a signal with a higher signal-to-noise ratio. If the long signal L for a given sample set exceeds the dynamic range, then the short signal S may be scaled in a manner described below in order to extrapolate or approximate what the long signal L value might be. In this instance, the scaled value of the short signal S is then used for subsequent signal analysis.

Figure 3:
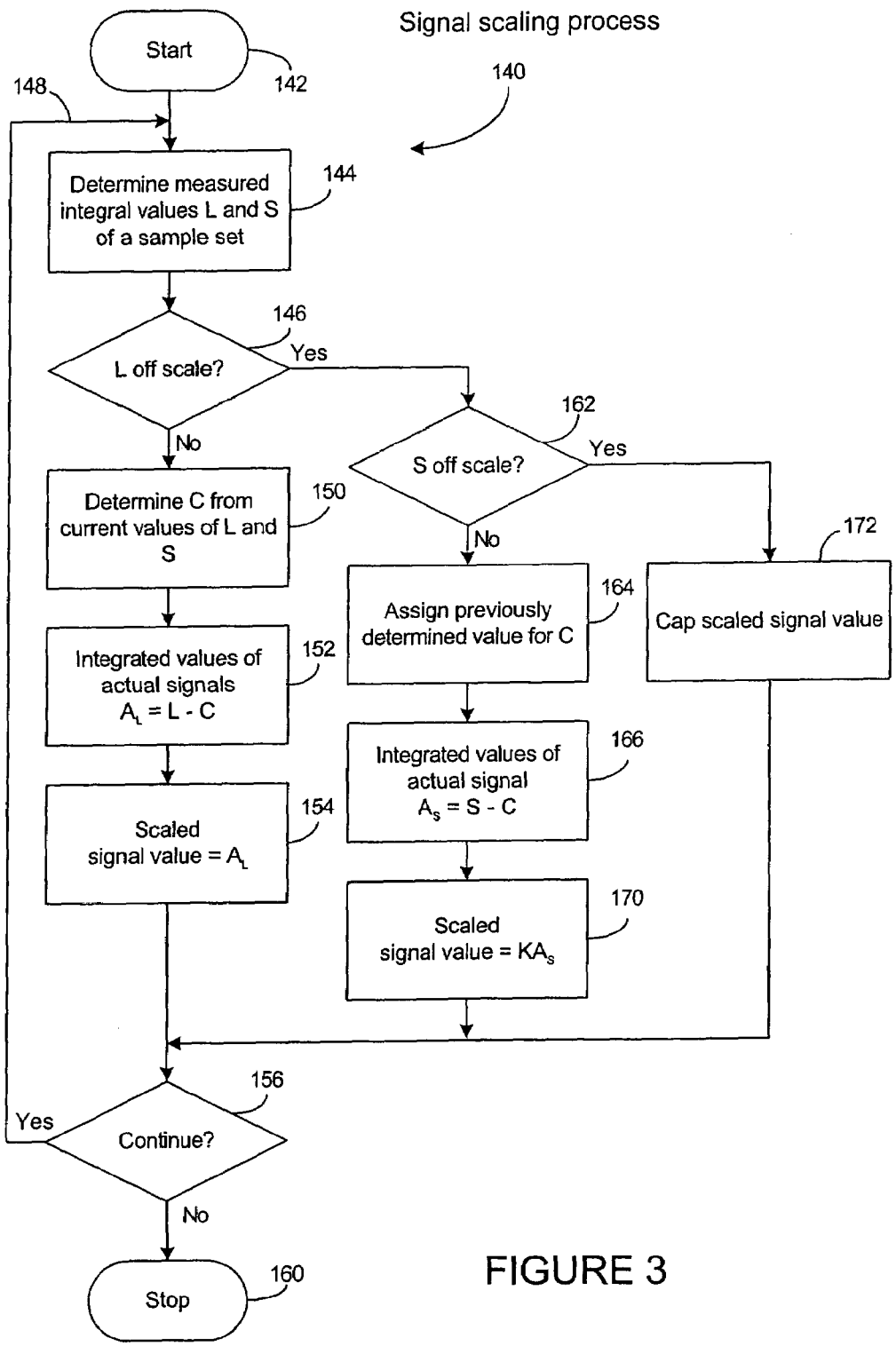
FIG. 3 illustrates a generalized signal scaling process that utilizes the long and short intervals from a sample set.

FIG. 3 illustrates a signal scaling process 140 that may be used to implement the aforementioned selective scaling approach. The process commences in a start state 142 and enters a loop 148 described below. In one aspect, the loop 148 cycles through an array or data structure that has been loaded with values for L and S acquired during CCD analysis of the sample. Alternatively, the loop 148 may progress in real time as analysis takes place. In state 144 of the loop 148, measured integral values of L and S of a sample set are determined. A decision state 146 that follows may be used to determine whether the value of L is off scale or exceeds the dynamic range of the instrumentation. In the instance where the dynamic range is not exceeded, L may be used for subsequent analysis as previously described. Thus in state 150, value of the offset C may be determined (according to Equation 4) from the measured values of L and S, along with the signal-specific value of the proportionality parameter K. In state 152 that follows, the offset C may be subtracted from the measured value of L to yield the actual signal $A_L$. In state 154 that follows, the scaled signal value that is to be used for subsequent analysis may be assigned the unscaled value of the actual signal $A_L$. The process 140 then determines in a decision state 156 whether the loop 148 should continue. If the loop 148 continues, then the process proceeds back to state 144 to initiate another cycle. If the loop 148 is complete, then the process terminates at a stop state 160.

In state 146, when the determination is made that the measured signal L exceeds the scaling limit, then it may be observed that the usefulness of the measured signal L is potentially limited, and thus the measured signal S may be processed and scaled so as to extrapolate as to where the actual long signal $A_L$ might be. When initiating this extrapolation process, another decision state 162 may be entered that determines if the measured signal S itself exceeds the dynamic range. In one aspect, if the measured signal is within the dynamic range, then it may be processed and scaled in the manner described below.

In state 164, a value for the offset C is determined. In one aspect, the measured signal L may not be used for the current sample set since the value of C determined by using Equation 4 may produce an off scale result. Hence in one implementation of the process, the value of C may be obtained from the previous or a recent sample set. Offset determination in this manner is desirable as in many CCD systems, the offset C does not fluctuate substantially. This is typically true if the operating conditions, such as temperature, are controlled. Thus, the approximation method in state 164 is one manner for determining the value of C. In state 166 that follows, the offset C may be subtracted from the measured signal S to generate the actual signal $A_S$. In state 170 that follows, the actual signal $A_S$ is scaled by a factor of K and may be assigned as the scaled signal value that is to be used for subsequent analysis. One method for determining the parameter K is described below. The process 140 then proceeds to the previously described decision state 156 to determine if the loop 148 should continue.

If the signal S is determined to be off scale in state 162, then both measured signals L and S may be considered off scale with regard to the dynamic range. In this instance, the process may identify each signal as having limited usefulness for the current sample set. In one implementation of the process, such off-scale measured signals may be "capped" or flagged in state 172 by a selected value so as to be easily recognizable during subsequent analysis. In one exemplary embodiment, the "actual" short signal $A_S$ may be assigned a value of M, where M is the upper limit value of the dynamic range (for example, a 13-bit ADC has a dynamic range of 0–8191, and M=8192). In this manner, the capped signal value may be greater than scaled signals that were derived from the within-scale measured signals. Such easy identification of off-scale signals may then be dealt with in an appropriate manner during the subsequent analysis.

Figure 4:
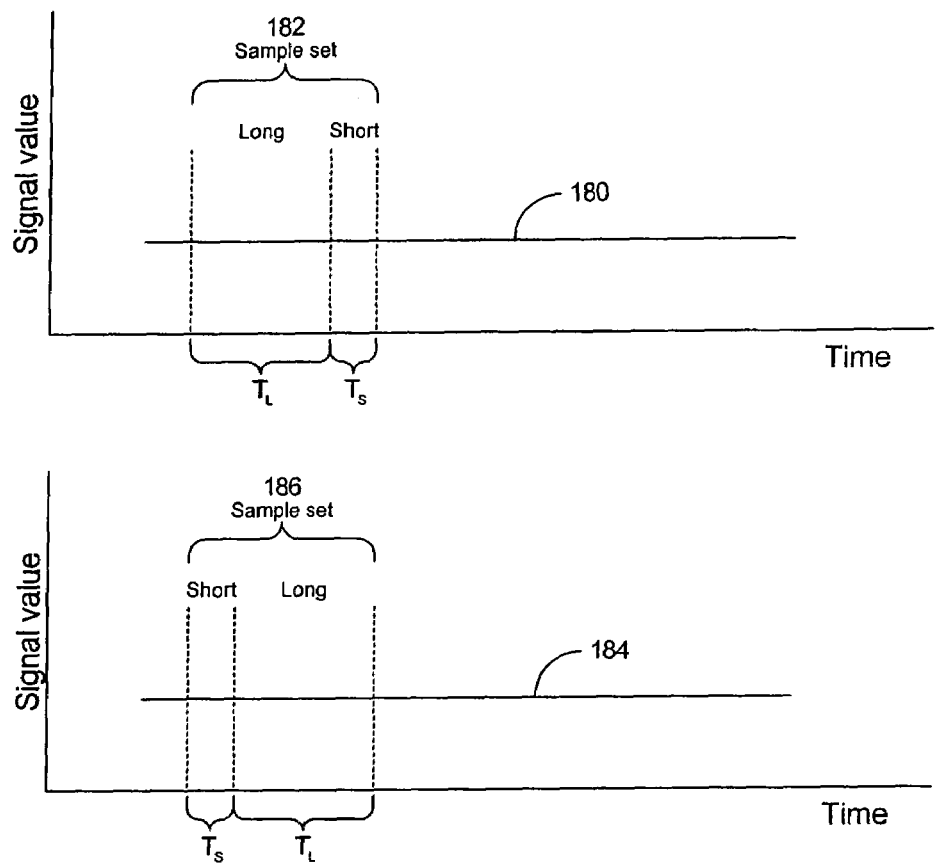
FIG. 4 illustrates one embodiment of the analysis of a sample set comprising adjacent long and short intervals.
Figure 5:
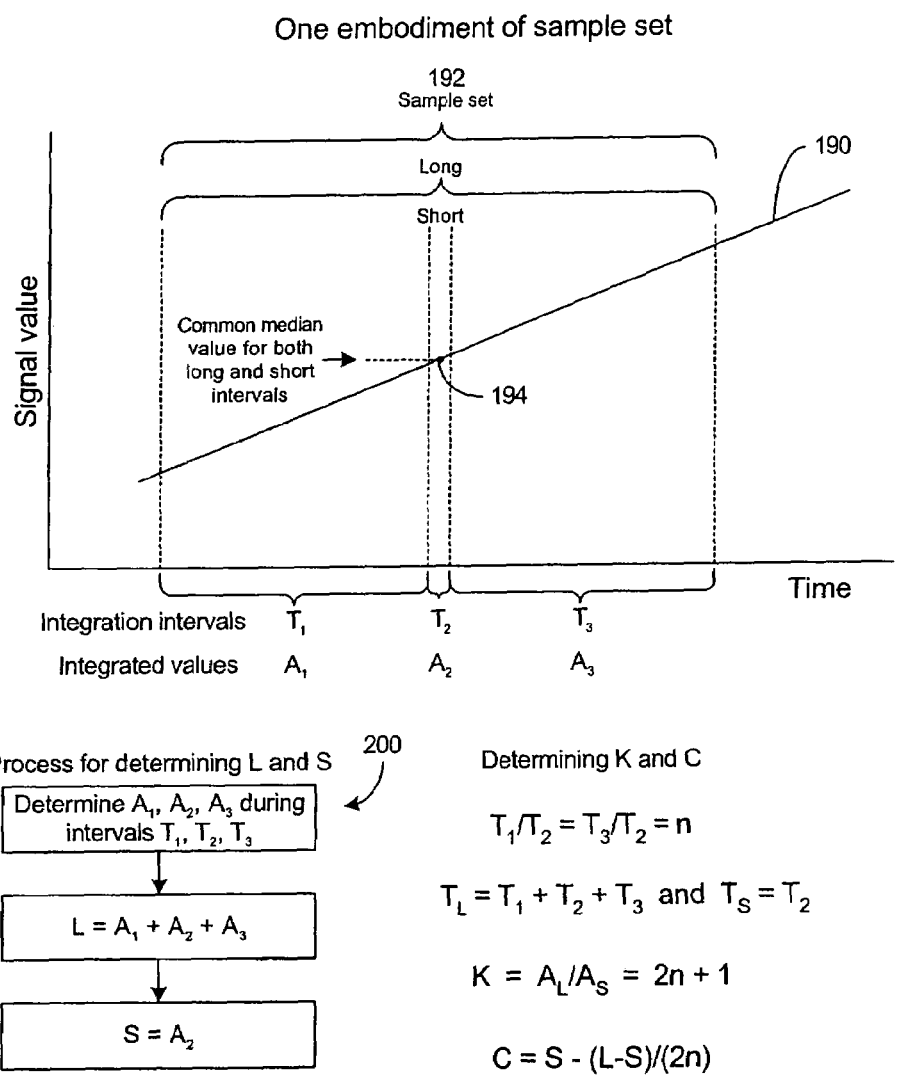
FIG. 5 illustrates another embodiment of the sample set comprising a short interval interposed between long intervals such that a short signal is obtained from the short interval and a long signal is obtained from the long-short-long intervals.
Figure 6:
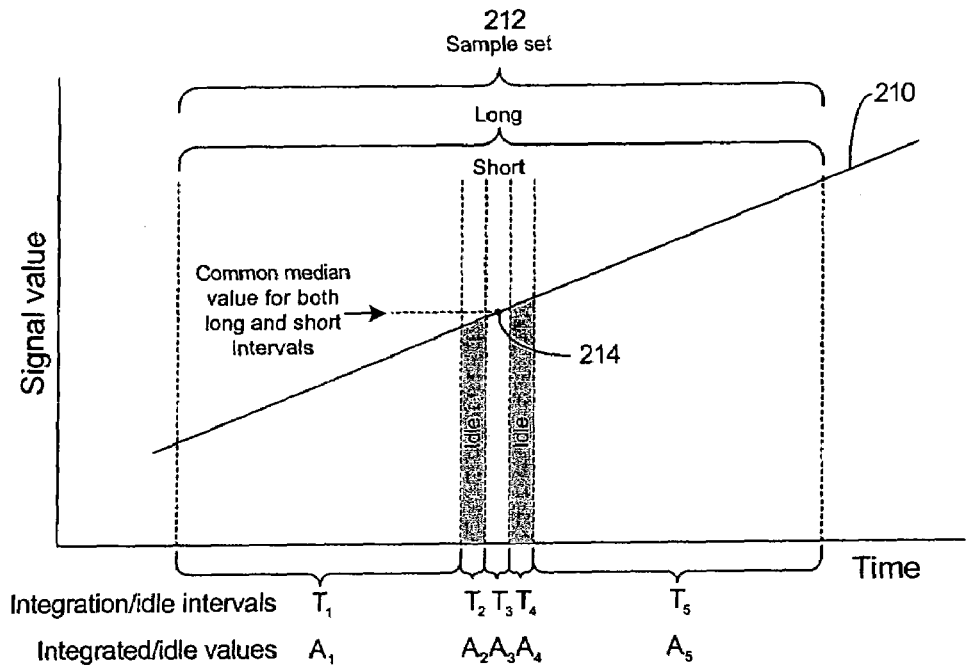
FIG. 6 illustrates another embodiment of the sample set including idle intervals interposed between integration intervals.
Figure 6:
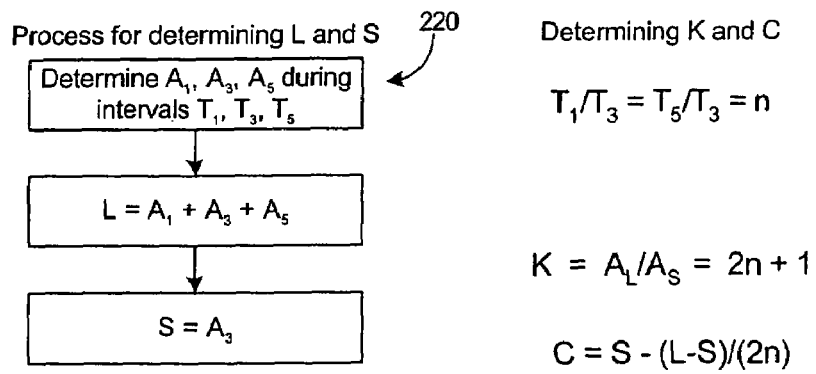

In one aspect, the sample set may comprise different combinations of the alternating short and long samples. FIGS. 4–6 illustrate various embodiments of the sample set and signal distribution characteristics. In each of the sample sets described hereinbelow, the measured signals L and S may be obtained in a sample set specific manner depending upon the characteristics of sampling. Furthermore, each sample set may be suited for a particular signal type resolution as described below. Thus the proportionality parameter K may be associated with a selected sample set to yield an operationally useful value in processing the signal information. In one aspect, determination of the sample set specific L, S, and K allows for determination of the scaled signal value described above in a generalized process in reference to FIG. 3.

As illustrated in FIG. 4, one embodiment of a sample set 182 comprises a combination of a long sample and an adjacent short sample. Alternatively, a sample set 186 may comprise a short sample followed by a long sample. Sample sets 182, 186 may be used when signals 180, 184, respectively, are either generally flat or change relatively slowly during the time interval associated with the sample sets. For such a signal, the integrated values of the actual signals $A_L$ and $A_S$ are directly proportional to their respective integration times $T_L$ and $T_S$. Thus, $T_L/T_S = A_L/A_S$, where the ratio $A_L/A_S$ is the definition of the proportionality parameter K (Equation 3). The integration time intervals may be selected such that $T_L$ is greater than $T_S$ by a factor of n, yielding $$K = n \tag{5a}$$

$$C = S - \frac{L-S}{n-1}. \tag{5b}$$

Hence, the offset C can be determined according to Equation 5b, thereby allowing the scaled signal value to be determined in a manner described above.

As illustrated in FIG. 5, another embodiment of a sample set 192 comprises a sequence of long-short-long sampling time intervals $T_1$, $T_2$, and $T_3$, with corresponding measured signals $A_1$, $A_2$, and $A_3$. The short sample comprises the measurement made during time interval $T_S=T_2$, and the long sample comprises the measurement made during time interval $T_L=T_1+T_2+T_3$. Thus, as illustrated in FIG. 5, a process 200 for determining the measured signals L and S comprises determining $A_1$, $A_2$, and $A_3$ during time intervals $T_1$, $T_2$, and $T_3$, the measured signal $L=A_1+A_2+A_3$, and the measured signal $S=A_2$.

In various embodiments, the sample set 192 may be configured such that $T_1=T_3$, and $T_1/T_2=T_3/T_2=n$, where n is a constant value. Given such a configuration, when a portion of a signal 190 encompassed by the sample set 192 is linear such as that shown in FIG. 5, a common median value 194 is shared by both the short and long samples temporally and in terms of the signal value. From such a symmetry, it can be demonstrated that $$K = \frac{A_L}{A_S} = 2n + 1 \tag{6a}$$

$$C = S - \frac{L-S}{2n}. \tag{6b}$$

Hence, the offset C can be determined according to Equation 6b, thereby allowing the scaled signal value to be determined in a manner described above. It will be appreciated that the sample set 192 illustrated in FIG. 5 may be used when the CCD signal is approximately linear, at least during the interval encompassed by the sample set. In the instance where the CCD signal is not substantially linear, a systematic variance may be generated, however, this variance may be within the acceptable range for a given measurement and analysis.

In various embodiments, each of the long intervals $T_1$ and $T_3$ is selected to be approximately half of a "standard" non-segmented integration time. The short interval $T_2$ is typically substantially smaller than $T_1$ or $T_3$, and is selected to achieve, by methods disclosed herein, a desired dynamic range. It will be appreciated that the duration of the long and short intervals may be determined by the existing hardware used in the sequence analysis system. These durations may be modifiable or fixed depending on the type of instrument used. One advantage to the present teachings is that the disclosed methods may be applied to signal information generated by most conventional systems in its raw form without necessitating hardware modifications to improve the dynamic range.

FIG. 6 illustrates another sample set 212 that accounts for the idle time intervals. In some respects, the sample set 212 is similar to the sample set 192 of FIG. 5, with the exception that an idle time interval may be interposed between two adjacent sampling intervals. As such, the sample set 212 comprises a sequence of time intervals $T_1$ to $T_5$, wherein T1 corresponds to a first long sample with measured signal $A_1$, $T_2$ corresponds to a first idle time interval, $T_3$ corresponds to a short sample with measured signal $A_3$, $T_4$ corresponds to a second idle time interval, and $T_5$ corresponds to a second long sample with measured signal $A_5$. In various embodiment, if a portion of a signal 210 encompassed by the sample set 212 is linear such as that shown in FIG. 6, $T_1=T_5$, and $T_2=T_4$, therefore, a common median value 214 may be shared by both the short and long samples temporally and/or in terms of the signal value. Using such a symmetry, it may be shown that the ratio $A_L/A_S=(T_1+T_3+T_5)/T_3$.

In one implementation, the sample set 212 may be configured such that $T_1/T_3=T_5/T_3=n$, where n is a constant value. Thus, $$K = \frac{A_L}{A_S} = 2n + 1 \tag{7a}$$

$$C = S - \frac{L-S}{2n}. \tag{7b}$$

Hence, the offset C can be determined according to Equation 7b, thereby allowing the scaled signal value to be determined in a manner similar to that described above. It will be appreciated that the sample set 212 illustrated in FIG. 6 may be used when the CCD signal 125 is approximately linear, at least during the interval encompassed by the sample set. While the CCD signal 125 may not be substantially linear thereby generating a systematic variance, such variances may be within the acceptable range for a given measurement and analysis.

It will be appreciated that the first and second idle time intervals $T_2$ and $T_4$ are desirably similar in order to preserve the symmetry of the long and short samples, and thus facilitate establishing the common median value 214. In one embodiment, the idle interval may be a function of the CCD 122 and its associated signal processing devices, with a range of approximately 1–10 ms. In one aspect, the idle intervals $T_2$ and $T_4$ are selected to be as short as possible, usually limited by camera hardware and/or control firmware. The long intervals $T_1$, $T_5$, and the short interval $T_3$ therebetween may be selected in a similar manner as that described above in reference to FIG. 5.

Figure 7:
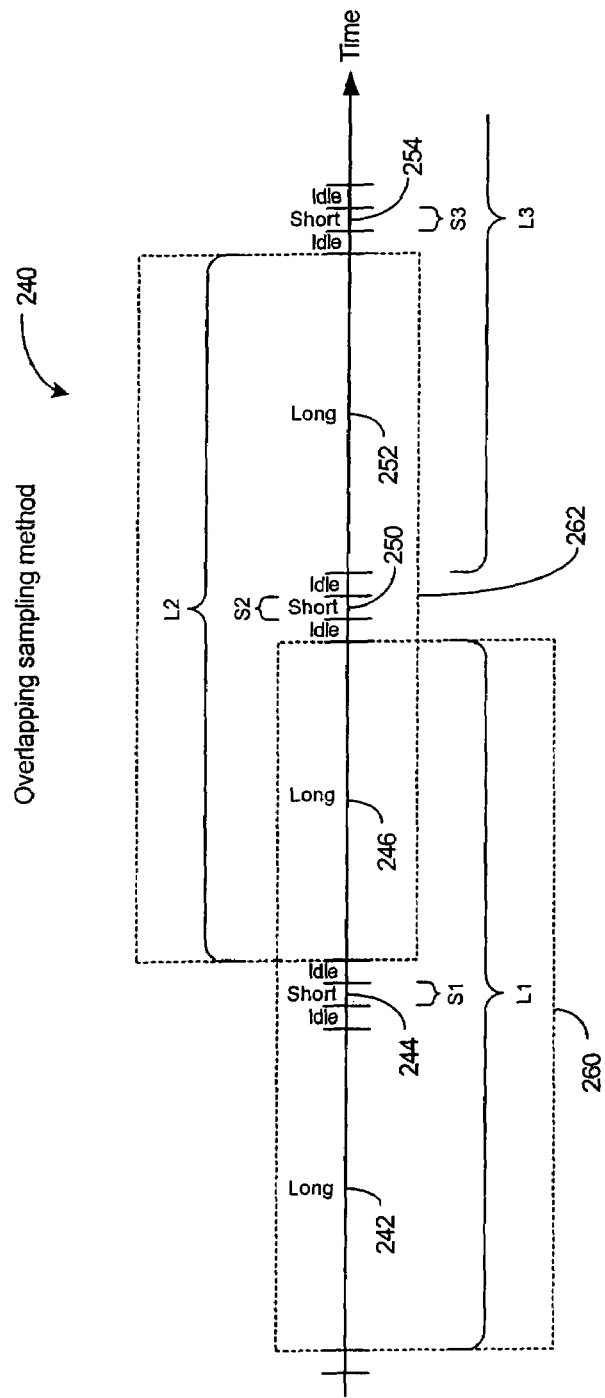
FIG. 7 illustrates an overlapping sampling method wherein portions of neighboring sample sets overlap to increase the number of sample sets.

The various implementations of the CCD signal scaling process described above are typically repeated for a plurality of sample sets during measurement of the fragments 100 for a given sample. In one aspect, a sampling method may include overlapping of the sample sets in a manner described below. FIG. 7 illustrates a series of alternating long and short integration intervals, with idle intervals interposed therebetween. It will be appreciated that while the sampling method of FIG. 7 is described in context of having the idle intervals, the sampling method is equally applicable to situations where the idle interval is either relatively small or substantially negligible.

In various embodiments, an overlapping sampling method 240 comprises a plurality of sample sets with each sample set having the short interval interposed between the two long intervals. Such a sample set is described above in reference to FIG. 6. An exemplary segment of CCD signal sampling comprises a sequence of long interval 242, short interval 244, long interval 246, short interval 250, long interval 252, and short interval 254.

A first exemplary sample set 260 comprises a short measured signal S1 obtained by integrating during the short interval 244 and a long measured signal L1 obtained by integrating during the intervals 242, 244, and 246. A second exemplary sample set 262 comprises a short measured signal S2 obtained by integrating during the short interval 250 and a long measured signal L2 obtained by integrating during the intervals 246, 250, and 252. Thus, the first and second sample sets 260 and 262 overlap in the long interval 246. Such an overlapping allows the number of samples sets (data points) to be increased for a given measurement pass. If the measurement pass comprises a total time interval having N non-overlapping sequential sample sets, the overlapping allows the number of sample sets to increase to approximately 2N.

In one aspect, the various long-short-long integration methods described above in reference to FIGS. 5–7 can be adapted to reduce the effects of noise (thereby increasing the signal to noise ratio) associated with the CCD camera. In FIGS. 5–7, the short integration time interval is interposed between two long integration time intervals, and the measured long signal is the sum of the integrated values during the long-short-long intervals (lsl method). As described below in greater detail, if a long signal is instead comprised of the two long integration time intervals and excludes the short interval (ll method), the signal to noise ratio (SNR) of the measurement can be increased.

Such a scheme, in reference to FIG. 5, yields in a similar manner described above, L=A1+A3, S=A2, K=2n, and C=S−(L−S)/(2n−1). When applied to the configuration illustrated in FIG. 6, this scheme yields L=A1+A5, S=A3, K=2n, and C=S−(L−S)/(2n−1).

One advantage attained by reducing the number of samplings in the long signal L (two instead of three) relates to the noise σ associated with the CCD. As is generally understood, the noise σ refers to an intrinsic uncertainty introduced during the process of quantifying the signal on the CCD and, in most cases, may be estimated as a square root of quadratures of it's main components—read noise $\sigma_R$ and shot noise $\sigma_S$. For on-scale signal, including the weak signal where the increase in SNR is particularly useful, the SNR can be expressed as $$SNR = \frac{A_L}{\sigma} = \frac{A_L}{\sqrt{\sigma_S^2 + \sigma_R^2}} = \frac{A_L}{\sqrt{A_L + \sigma_R^2}} \qquad (8)$$

where $A_L$ represents the actual signal and a represents the overall noise during the measurement. And since the shot noise as follows Poisson statistics, $\sigma_S^2 = A_L$.

For the lsl and ll methods illustrated in FIGS. 5–7, each of the two long intervals is approximately n times as long as the short interval. Hence, $$A_{lsl} = \frac{2 \cdot n + 1}{2 \cdot n} \cdot A_{ll},$$

where $A_{lsl}$ is the actual signal for the lsl method and $A_{ll}$ is the actual signal for the ll method. Furthermore, the lsl method integrates during three separate time intervals such that the individual interval noises add in quadrature to yield $\sigma_{lsl}^2 = 3\sigma_R^2 + A_{lsl}$; similarly, the ll method integrates during two separate time intervals, yielding $\sigma_{ll}^2 = 2\sigma_R^2 + A_{ll}$. Thus, a ratio of SNR for the ll and lsl configurations can be expressed as $$\frac{SNR_{ll}}{SNR_{lsl}} = \frac{2n}{2n+1} \sqrt{\frac{3\sigma_R^2 + A_{ll}\frac{2n+1}{2n}}{2\sigma_R^2 + A_{ll}}}. \qquad (9)$$

For a typical operating configuration where n=20, $A_{ll}$=8000 electrons, and $\sigma_R$=80 electrons rms, the ratio $SNR_{ll}/SNR_{lsl}$=1.12, indicating an approximately 12% increase in the signal to noise ratio. As indicated in Equation 9, the ratio $SNR_{ll}/SNR_{lsl}$ can be increased further by selecting a different values n, $A_L$, $\sigma_R$, or any combination thereof.

Although the above-disclosed embodiments of the present invention have shown, described, and pointed out the fundamental novel features of the invention as applied to the above-disclosed embodiments, it should be understood that various omissions, substitutions, and changes in the form of the detail of the devices, systems, and/or methods illustrated may be made by those skilled in the art without departing from the scope of the present invention. Consequently, the scope of the invention should not be limited to the foregoing description, but should be defined by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

What is claimed is:

1. A method of sampling a photo-detector signal, the method comprising:
    performing a series of integrations of the photo-detector signal wherein the series comprises alternating long and short integration intervals; and
    forming a plurality of overlapping sample sets wherein each sample set comprises integrations performed during at least one long interval to yield a first signal value and at least one short interval to yield a second signal value and wherein each sample set overlaps with its neighboring sample set by at least one of the long or short intervals.

2. The method of claim 1, wherein the sample set comprises integrations performed during a sequence of long-short-long time intervals so as to overlap with its neighboring sample set by at least one of the long intervals thereby increasing the number of sample sets obtained from the series of integrations.

3. The method of claim 2, wherein the sample set further comprises idle intervals so as to yield a sequence of long-idle-short-idle-long intervals.

4. The method of claim 2, wherein the first signal value comprises a sum of integrations of the photo-detector signal performed during the long-short-long intervals, and wherein the second signal value comprises the integration of the photo-detector signal performed during the short interval such that the first and second signal values share a common median time value.

5. The method of claim 4, wherein for an approximately linear photo-detector signal, the common median time value of the first and second signal values allow the second signal value to be scaled to the first signal value when the first signal value exceeds a specified dynamic range.

6. The method of claim 2, wherein the first signal value comprises a sum of integrations of the photo-detector signal performed during the two long intervals while excluding the short interval, and wherein the second signal value comprises the integration of the photo-detector signal performed during the short interval such that the first and second signal values share a common median time value.

7. The method of claim 1, wherein a signal to noise ratio associated with the first signal value is improved by excluding a noise associated with the photo-detector signal during the short interval, wherein the noise includes a shot noise and a read noise.

8. The method of claim 1, wherein the photo-detector signal comprises a CCD, a photomultiplier, or a semiconductor based device.

* * * * *

UNITED STATES PATENT AND TRADEMARK OFFICE
CERTIFICATE OF CORRECTION

| | | |
|---|---|---|
| PATENT NO. | : 7,067,791 B2 | Page 1 of 1 |
| APPLICATION NO. | : 11/059740 | |
| DATED | : June 27, 2006 | |
| INVENTOR(S) | : Dmitry M. Sagatelyan et al. | |

It is certified that error appears in the above-identified patent and that said Letters Patent is hereby corrected as shown below:

On Title Page, Item (73) (Assignee), Line 1, delete " Cororation, " and insert -- Corporation, --, therefor.

In Column 1, Line 8, after "2002" insert -- , --.

In Column 11, Line 46 (approx.), delete -- a -- and insert -- $\sigma$ --, therefor.

In Column 11, Line 48 (approx.), delete -- as -- and insert -- $\sigma_s$ --, therefor.

Signed and Sealed this

Tenth Day of April, 2007

JON W. DUDAS
*Director of the United States Patent and Trademark Office*